US010653839B2

(12) United States Patent
Vigot et al.

(10) Patent No.: US 10,653,839 B2
(45) Date of Patent: May 19, 2020

(54) NEEDLELESS INJECTION DEVICE WITH SLIDING MEMBRANE

(71) Applicant: CROSSJECT, Dijon (FR)

(72) Inventors: Xavier Vigot, Veronnes (FR); Christophe Auriel, Binges (FR)

(73) Assignee: CROSSJECT, Dijon (FR)

( * ) Notice: Subject to any disclaimer, the term of this patent is extended or adjusted under 35 U.S.C. 154(b) by 157 days.

(21) Appl. No.: 16/103,510

(22) Filed: Aug. 14, 2018

(65) Prior Publication Data
US 2018/0344931 A1  Dec. 6, 2018

Related U.S. Application Data

(63) Continuation of application No. PCT/FR2017/050322, filed on Feb. 13, 2017.

(30) Foreign Application Priority Data

Feb. 18, 2016 (FR) ...................................... 16 51340

(51) Int. Cl.
A61M 5/20 (2006.01)
A61M 5/30 (2006.01)
A61M 5/315 (2006.01)
A61M 5/28 (2006.01)
A61M 5/31 (2006.01)

(52) U.S. Cl.
CPC ........ A61M 5/2046 (2013.01); A61M 5/2053 (2013.01); A61M 5/282 (2013.01); A61M 5/30 (2013.01); A61M 5/31513 (2013.01); A61M 5/31 (2013.01); A61M 2005/2006 (2013.01); A61M 2005/2073 (2013.01)

(58) Field of Classification Search
CPC ............ A61M 5/2046; A61M 5/31513; A61M 5/282; A61M 5/2053; A61M 5/30; A61M 5/31; A61M 2005/2006; A61M 2005/2073
See application file for complete search history.

(56) References Cited

U.S. PATENT DOCUMENTS

2006/0089595 A1 * 4/2006 Alexandre .............. A61M 5/30
                                                            604/69

FOREIGN PATENT DOCUMENTS

CH      580427     10/1976
FR      2815544    4/2002
FR      2852516    9/2004

OTHER PUBLICATIONS

International Search Report for international application PCT/FR2017/050322, dated May 26, 2017.

* cited by examiner

Primary Examiner — Amber R Stiles
(74) Attorney, Agent, or Firm — Burris Law, PLLC

(57) ABSTRACT

The present disclosure concerns a needleless injection device including a body forming a housing, a gas generator, a tubular reservoir which contains an active ingredient to be injected, and a generally T-shaped elastically deformable membrane. The membrane includes a tubular portion which extends axially in the reservoir and is designed to lie axially in the reservoir under the effect of the pressure generated by the gas generator. A nozzle for injecting the active ingredient is arranged at the lower end of the reservoir. The device further includes a sock which wraps the tubular portion of the membrane, at least partially. The sock is adapted to limit the friction between the tubular portion of the membrane and the reservoir.

9 Claims, 2 Drawing Sheets

NEEDLELESS INJECTION DEVICE WITH SLIDING MEMBRANE

CROSS-REFERENCE TO RELATED APPLICATIONS

This application is a continuation of International Application No. PCT/FR2017/050322, filed on Feb. 13, 2017, which claims priority to and the benefit of FR 16/51340 filed on Feb. 18, 2016. The disclosures of the above applications are incorporated herein by reference.

FIELD

The present disclosure relates to a needleless injection device.

BACKGROUND

The statements in this section merely provide background information related to the present disclosure and may not constitute prior art.

The technical field of the present disclosure is that of the needleless, pre-filled and disposable injection devices, operating with an energy source such as for example a gas generator, and used for the intradermal, subcutaneous and intramuscular injections of liquid active ingredient for therapeutic use in human or veterinary medicine.

The active ingredient is constituted by a more or less viscous liquid, a mixture of liquid, or a gel. The active ingredient may also be a solid dissolved in a solvent suitable for the injection or be constituted of a powdery solid suspended at a certain concentration in a suitable liquid. The particle size of the active ingredient must then be compatible with the diameter of the ducts to avoid sealing them.

An injection device includes, in a known manner, as for example in the patent application FR-A-2815544 (equivalent to WO 02/34317), a body successively comprising a gas generator, an expansion chamber, a reservoir containing the liquid active ingredient and an injection system.

The reservoir is constituted by a glass tube which is inserted into a tubular housing delimited by the body of the device, the tube being sealed by an upstream piston and a downstream piston between which the liquid active ingredient is contained.

The free downstream or lower end of the reservoir cooperates with an injection nozzle which delimits at least one injection channel extending axially along an injection axis.

The injection nozzle is delimited axially by an upper face axially bearing on the reservoir, and a lower injection face adapted to cooperate with a closure cap.

Furthermore, the injection device includes a hollow cover which wraps the body and which delimits a lower opening adapted for the passage of the injection nozzle.

In order to allow the injection of the active ingredient, the body is slidably mounted in the cover, from bottom to top along a sliding axis, between a rest position and an injection position, the driving of the body being carried out when the user presses the injection nozzle on his skin.

The displacement of the body in the cover allows the triggering of the gas generator, generating a pressurized gas which drives the pistons in displacement to inject the active ingredient through the skin of the patient, by passing through the injection nozzle.

There is known an injection device which is equipped with a generally T-shaped elastically deformable membrane, which comprises a radial annular disc which is interposed axially between the upper end of the reservoir and a seat formed by the body, and a tubular portion which extends axially in the reservoir, from the annular disc.

The tubular portion of the membrane is designed to extend axially under the effect of the pressurized gas, in order to drive the pistons in displacement.

The pressure of the gas also deforms the membrane radially, such that the membrane engages on the inner wall of the glass reservoir.

The friction between the membrane, which is generally made of elastomer, and the glass wall of the reservoir, is significant and absorbs a significant portion of the energy required for the elongation and extension of the tubular portion of the membrane in the reservoir.

In order to overcome this issue, it is known to lubricate the membrane in order to limit the friction between the membrane and the reservoir.

Although effective, the lubrication is a restrictive step during the production and assembly of the injection device.

SUMMARY

The present disclosure relates to a needleless injection device including:
 a body forming a housing;
 a gas generator;
 a tubular reservoir which contains an active ingredient to be injected, the reservoir extending axially in said housing from an upper end, to a lower end;
 a generally T-shaped elastically deformable membrane, the membrane comprising a tubular portion which extends axially in the reservoir and which is designed to lie axially in the reservoir under the effect of the pressure generated by the gas generator; and
 an injection nozzle for injecting the active ingredient which is arranged at the lower end of the reservoir, said device being characterized in that it includes a sock which wraps the tubular portion of the membrane at least partially, the sock being adapted to limit the friction between the tubular portion of the membrane and the reservoir.

The present disclosure allows limiting the energy absorbed by the friction between the membrane and the reservoir, in order to obtain a jet pressure through the satisfactory nozzle.

It can be seen that the sock improves the power of the active ingredient jet at the outlet of the nozzle.

The sock also promotes the deployment and the elongation of the membrane in the reservoir.

According to another feature, the sock has the shape of a sleeve which comprises:
 a cylindrical wall which extends axially and which is radially interposed between an inner wall of the reservoir and the tubular portion of the membrane; and
 a bottom which obstructs the sock.

The cylindrical shape of the sock, complementary to the shape of the reservoir, promotes the sliding of the sleeve in the reservoir.

According to another feature, to reduce friction, the sock is made of a material which has a coefficient of friction lower than the coefficient of friction of the material used to make the membrane.

In one form, the membrane is made of an elastomer-based material.

According to an exemplary form, the sock is made of plastic.

According to an exemplary form of the present disclosure, the sock is rigid enough not to be deformed radially under the effect of the pressure generated by the gas generator.

This feature aims to limit the contact surface between the sock and the reservoir, in order to limit the friction.

According to an exemplary form of the present disclosure, the membrane comprises a radial annular disk which is connected on the tubular portion of the membrane, the annular disc axially bearing on an upper end of the reservoir.

According to another feature, the sock is slidably mounted in the reservoir and has a diameter substantially smaller than the diameter of the inner wall of the reservoir.

According to another feature, the active ingredient contained in the reservoir is selected from the group comprising the following active ingredients:

Methotrexate,
Adrenaline,
Sumatriptan,
Hydrocortisone,
Naloxone,
Midazolam,
Apomorphine,
Ethylnatrexone bromide,
Phytomenadione,
Chlorpromazine hydrochloride,
Zuclopenthixol acetate,
Danaparoid sodium,
Enoxaparin sodium,
Estradiol cypionate,
Medoxyprogesterone acetate,
Medroparin calcium,
Methylprednisolone acetate
Heparin calcium, and
Terbulin.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
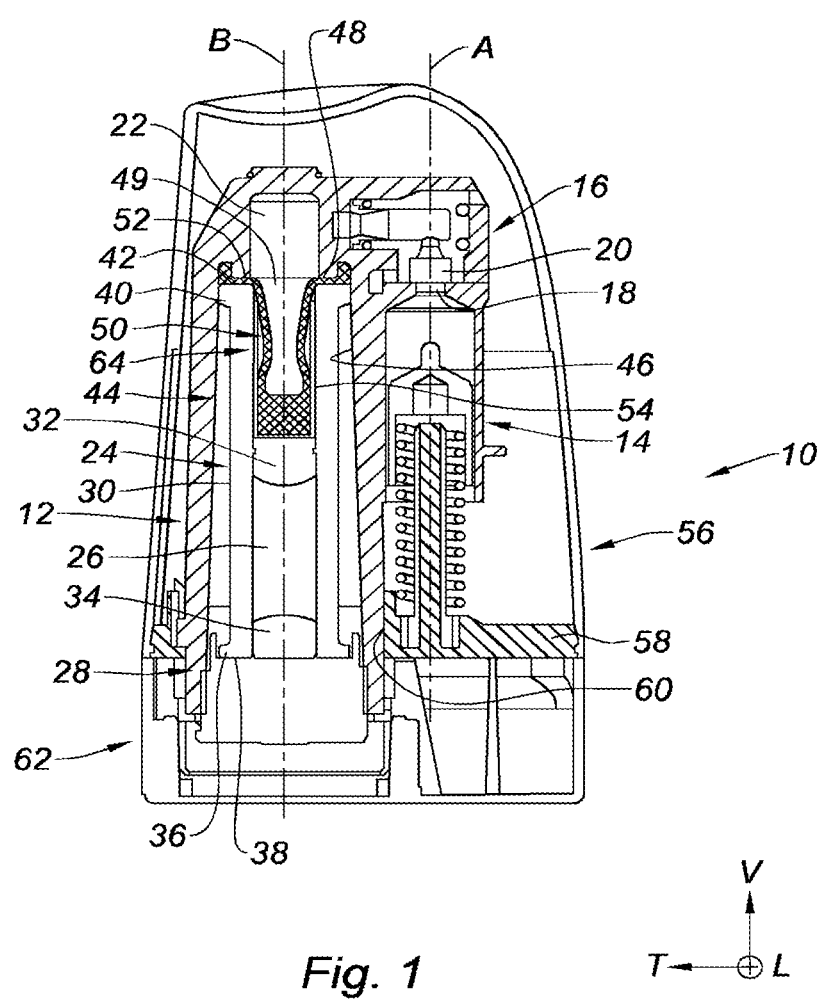
FIG. 1 is an axial sectional view which illustrates an injection device including a sock wrapping a membrane in a rest position according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the present disclosure, in order to clarify the description and claims, the longitudinal, vertical and transverse terminology will be adopted in a non-limiting way with reference to the trihedron L, V, T indicated in the figures.

Furthermore, in the present disclosure, the terms "upper," "lower," "horizontal," "vertical," and their derivatives refer to the position or the orientation of an element or a component, this position or this orientation being considered with reference to the orientation of the device in the figures and to the trihedron L, V, T, without reference to Earth's gravity.

Similarly, the terms "axial" and "radial" should be understood with reference to the injection axis B of the injection device.

FIG. 1 shows a needleless injection device 10, or needleless syringe, which includes a U-shaped body 12 successively comprising a percussion device 14, a gas generator 16 comprising a primer 18 and a pyrotechnic charge 20, an expansion chamber 22, a reservoir 24 containing the liquid active ingredient 26 and an injection nozzle 28.

The percussion device 14 and the gas generator 16 constitute a first linear subassembly of the body 12 which extends axially along a vertical sliding axis A, and the reservoir 24 containing the active ingredient 26 and the injection nozzle 28 form a second linear subassembly of the body 12 which extends axially along a second vertical injection axis B.

These two subassemblies are connected to each other by the expansion chamber 22 which has an axis perpendicular to the axes A, B of the subassemblies.

The reservoir 24 is constituted by a glass tube 30 sealed by an upstream piston 32 and a downstream piston 34 between which the liquid active ingredient 26 is contained, the pistons being made of an elastically deformable elastomer-based material.

The reservoir 24 extends axially from a lower flange 36 which has an annular lower face 38 arranged facing the injection nozzle 28, to an upper flange 40 having an annular upper face 42.

The reservoir 24 is arranged in a housing 44 formed by the body 12, housing 44 which is delimited radially by a tubular wall 46 which extends about the injection axis B.

The housing 44 extends axially from an upper radial seat 48 which is formed by the body 12 and which delimits an outlet orifice 49 of the expansion chamber 22.

According to one form, the body 12 is made by plastic injection molding.

Figure 2:
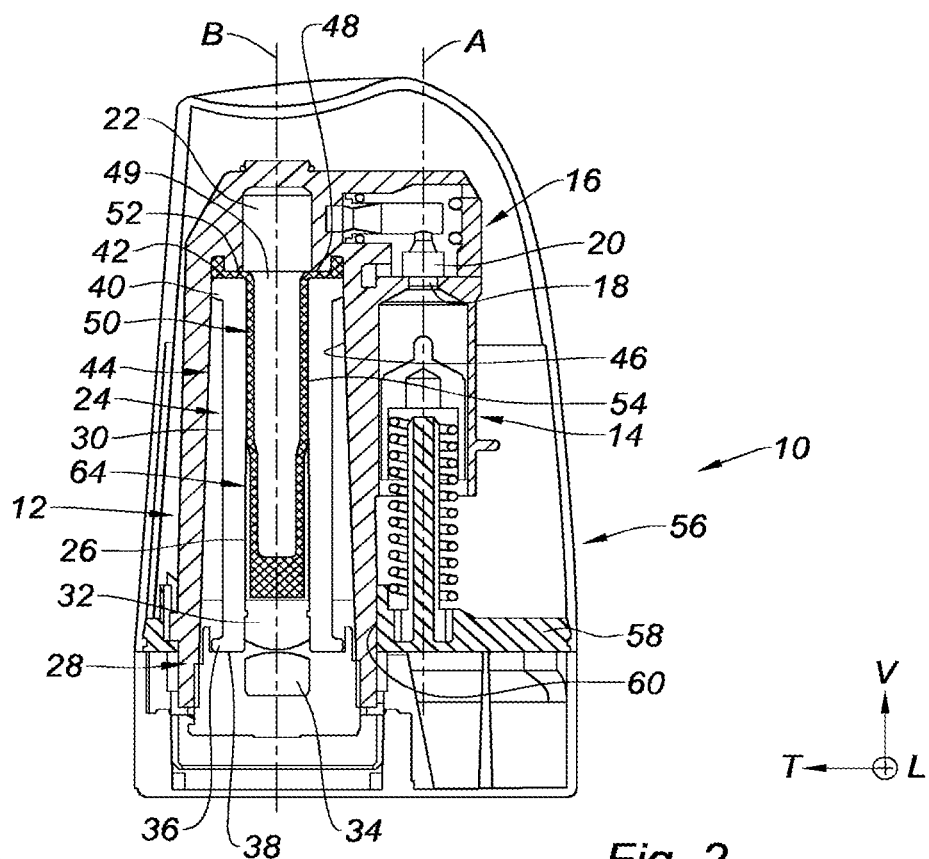
FIG. 2 is an axial sectional view which illustrates the injection device of FIG. 1 with the membrane in an extended position.

Also, according to FIGS. 1 and 2, the device 10 is equipped with a generally T-shaped elastically deformable membrane 50, which comprises a radial annular disc 52 which is interposed axially between the upper flange 40 of the reservoir 24 and the seat 48 formed by the body 12, and a tubular portion 54 which extends axially in the reservoir 24, from the annular disk 52.

As seen in FIG. 2, the tubular portion 54 of the membrane 50 is designed to extend axially, under the effect of the pressure of the gas generated by the gas generator 16, to push the upstream piston 32 downwards in order to eject the active ingredient 26 through the injection nozzle 28.

To this end, the membrane 50 is made of an elastomer-based material.

With reference to FIG. 1, the body 12 is wrapped by a hollow cover 56 which delimits a lower opening closed by a horizontal soleplate 58 forming a bottom of the cover.

The soleplate 58 delimits a circular passage 60 about the injection axis B which is adapted for the passage of the injection nozzle 28 and the downstream end of the body 12, such that the nozzle 28 includes a lower section protruding vertically downwards out of the cover 56.

More particularly, the nozzle 28 is screwed onto a free end emerging from the housing 44 formed by the body 12, the nozzle 28 compressing axially the assembly formed by the reservoir 24 and the membrane 50 on the seat 48 of the housing 44.

Also, the injection device 10 is equipped with a plug 62 which is removably mounted on the body 12 by a bayonet-type locking means.

Figure 4:
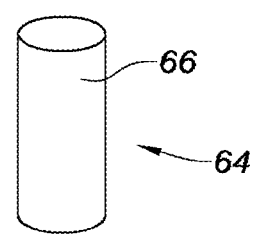
FIG. 4 is a detailed perspective view illustrating the cylindrical sock of FIG. 1.

In accordance with the present disclosure, the device 10 includes a sock 64, shown in detail in FIG. 4, which wraps the tubular portion 54 of the membrane 50.

Figure 3:
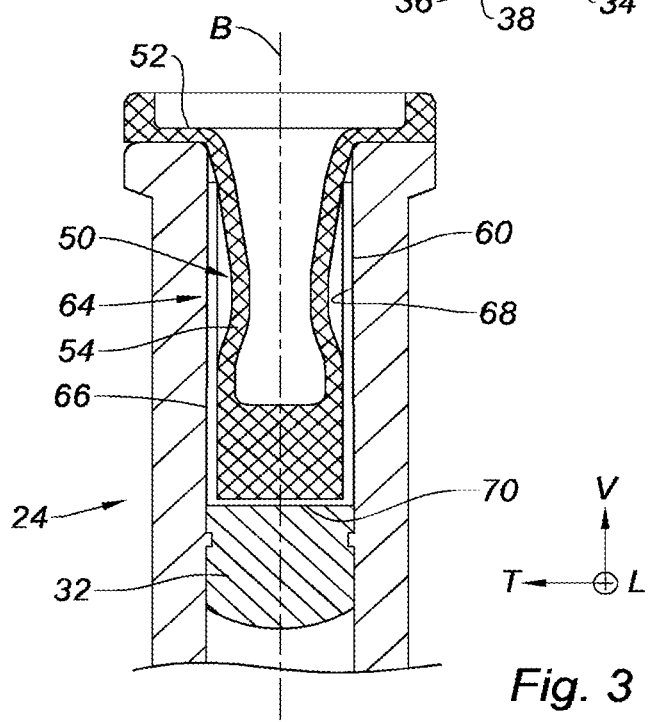
FIG. 3 is a detailed axial sectional view illustrating the membrane and the sock of FIG. 1.

As seen in FIG. 3, the sock 64 has the shape of a sleeve which comprises a cylindrical wall 66 which extends axially along the injection axis B and which is interposed radially between the inner wall 68 of the reservoir 24 and the tubular portion 54 of the membrane 50.

Also, the sock 64 includes a disk-shaped bottom 70 which axially obstructs the sock 64 in its lower portion.

The bottom 70 of the sock 64 may have a vertical thickness which varies depending on the volume of the active ingredient 26 contained in the reservoir 24. Thus, the more the volume of active ingredient is reduced, the greater the thickness of the bottom 70 of the sock 64 will be, the extra-thickness of the sock compensating for the volume of active ingredient.

The sock 64 is made of a material which has a coefficient of friction lower than the coefficient of friction of the material used to make the membrane 50, in order to allow the sock 64 to limit the friction between the tubular portion 54 of the membrane 50 and the reservoir 24.

According to an exemplary form, the sock 64 is made of smooth plastic.

Without limitation, the sock may also be made of aluminum or any other material having a low coefficient of friction on the glass.

When the gas generator 16 is activated, the pressurized gas enters the membrane 50 and the tubular portion 54 of the membrane 50 extends axially downwards under the effect of the pressure generated by the gas, and simultaneously, the sock 64 is driven in axial sliding downwards with the tubular portion 54 of the membrane 50.

Thus, the sock 64, thanks to its reduced coefficient of friction, slides on the inner wall 68 of the reservoir 24 to promote the axial elongation of the membrane 50.

According to another aspect of the present disclosure, the sock 64 is rigid enough not to be deformed, or little, radially under the effect of the pressure generated by the gas generator 16, in order to limit the contact and friction between the sock 64 and the reservoir 24.

For this purpose, the sock 64 can be made of aluminum for example.

As an exemplary form, a sock 64 made of aluminum has an inner diameter of 6 millimeters and an outer diameter of 6.8 millimeters to be rigid. Also, a sock 64 made of fiber-reinforced polyamide has an inner diameter of 5.4 millimeters and an outer diameter of 6.8 millimeters to be rigid.

In a complementary manner, the sock 64 is slidably mounted in the reservoir 24 and has a diameter substantially smaller than the diameter of the inner wall 68 of the reservoir 24.

These features allow limiting the contact surface, and therefore the friction, between the sock 64 and the reservoir 24 during the elongation of the membrane 50.

According to another aspect of the present disclosure, the active ingredient 26 contained in the reservoir 24 is selected from the group comprising the following active ingredients: Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medoxyprogesterone acetate, Medroparin calcium, Methylprednisolone acetate, Heparin calcium, and Terbulin.

The description of the present disclosure is given by way of non-limiting example.

It will be understood in particular that the sock 64 may have a length equal to or greater than the axial length of the tubular portion 54 of the membrane 50.

As used herein, the phrase "at least one of A, B, and C" should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device including:
a body forming a housing;
a gas generator;
a tubular reservoir that contains an active ingredient to be injected, the tubular reservoir extending axially in the housing from an upper end, to a lower end;
a T-shaped elastically deformable membrane comprising a tubular portion configured to extend and lie axially in the tubular reservoir under an effect of a pressure generated by the gas generator;
an injection nozzle for injecting the active ingredient arranged at the lower end of the tubular reservoir; and
a sock that at least partially wraps the tubular portion of the membrane and is adapted to limit friction between the tubular portion of the membrane and the tubular reservoir.

2. The needleless injection device according to claim 1, wherein the sock is sleeve shaped and comprises:
a cylindrical wall that extends axially and is radially interposed between an inner wall of the tubular reservoir and the tubular portion of the membrane; and
a bottom.

3. The needleless injection device according to claim 1, wherein the sock is made of a material having a coefficient of friction lower than a coefficient of friction of a material of the membrane.

4. The needleless injection device according to claim 1, wherein the membrane is made of an elastomer-based material.

5. The needleless injection device according to claim 1, wherein the sock is made of plastic.

6. The needleless injection device according to claim 1, wherein the sock is configured to not radially deform under the effect of the pressure generated by the gas generator.

7. The needleless injection device according to claim 1, wherein the membrane comprises a radial annular disk that is connected on the tubular portion of the membrane, the radial annular disc axially bearing on an upper end of the tubular reservoir.

8. The needleless injection device according to claim 1, wherein the sock is slidably mounted in the tubular reservoir and a diameter of the sock is substantially smaller than a diameter of an inner wall of the tubular reservoir.

9. The needleless injection device according to claim 1, wherein the active ingredient contained in the reservoir is selected from the group consisting of Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medoxyprogesterone acetate, Medroparin calcium, Methylprednisolone acetate Heparin calcium, and Terbulin.

* * * * *